US006893830B1

(12) United States Patent (10) Patent No.: US 6,893,830 B1
Janowski et al. (45) Date of Patent: May 17, 2005

(54) METHOD OF SCREENING OXYSTEROL ACTIVATION OF LXRα

(75) Inventors: Bethany A. Janowski, Dallas, TX (US); David John Mangelsdorf, Duncanville, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 596 days.

(21) Appl. No.: 09/603,131

(22) Filed: Jun. 23, 2000

Related U.S. Application Data

(63) Continuation of application No. 08/943,936, filed on Sep. 26, 1997, now abandoned.
(60) Provisional application No. 60/026,796, filed on Sep. 27, 1996.

(51) Int. Cl.$^7$ ..................... G01N 33/53; G01N 33/566; G01N 33/74; G01N 33/92
(52) U.S. Cl. .......................... 435/7.8; 435/7.1; 435/7.2; 435/11; 435/69.1
(58) Field of Search .......................... 435/7.1, 7.8, 7.2, 435/11, 69.1

(56) References Cited

U.S. PATENT DOCUMENTS

| | | | |
|---|---|---|---|
| 5,514,578 A | * | 5/1996 | Hogness et al. |
| 5,571,696 A | | 11/1996 | Evans et al. |
| 5,696,233 A | | 12/1997 | Evans et al. |
| 5,707,800 A | | 1/1998 | Mangelsdorf et al. |
| 5,710,004 A | | 1/1998 | Evans et al. |
| 5,723,329 A | | 3/1998 | Mangelsdorf et al. |
| 5,747,661 A | | 5/1998 | Evans et al. |

OTHER PUBLICATIONS

Baker et al., "Cloning and expression of full-length cDNA encoding human vitamin D receptor," *Proc. Natl. Acad. Sci. USA*, 85:3294–3298, 1988.
Byskov et al., "Chemical structure of sterois that activate oocyte meiosis," *Nature*, 374:559–562, 1995.
Dhar et al., "Biosynthesis of cholest–5–ene–3β, 24–diol (cerebrosterol) by bovine cerebral cortical microsomes," *J. Neurochem*, 21:51–60, 1973.
Dixon et al., "The isolation of crystalline 22r–hydroxycholestrerol and 20α,22r–dihydroxycholesterol from bovine adrenals," *Biochem. Biophys Res. Commun.*, 40:161–165, 1970.
Dolle et al., "Synthesis of zymosterol, fecosterol, and related biosynthetic sterol intermediates," *J. Am. Chem. Soc.*, 111:278–284, 1989.
Forman et al., "Identification of a nuclear receptor that is activated by farnesol metabolites," *Cell*, 81:687–693, 1995.
Forman et al., "15–deoxy–$\Delta^{12, 14}$–prostaglandin $J_2$ is a ligand for the adipocyte determination factor ppary," *Cell*, 83:803–812, 1995.

Giguere et al., "Identification of a receptor for the morphogen retinoic acid," *Nature*, 330:624–629, 1987.
Green et al., "Human oestrogen receptor cDNA: sequence, expression and homology to v–erb–A," *Nature*, 320:134–139, 1986.
Harmon et al., "Activiation of Mammalian retinoid X receptors by the insect growth regulator methoprene," *Proc. Natl. Acad. Sci. USA*, 92:6157–6160, 1995.
Heyman et al., "9–Cis retinoic acid is a high affinity ligand for the retinoid x receptor," *Cell*, 68:397–406, 1992.
Hollenberg et al., "Primary structure and expression of a functional human glucocorticoid receptor cDNA," *Nature*, 318:635–641, 1985.
Ikekawa, "Structures, biosynthesis and function of sterols in invertebrates," In: *Sterols and Bile Acids*, Danielsson, ed., Elsevier/N. Holland Biomedical Press, Amsterdam, pp. 199–230, 1985.
Issemann and Green, "Activiation of a member of the steroid hormone receptor superfamily by peroxisome proliferators," *Nature*, 347:645–650, 1990.
Janowski et al., "An oxysterol signalling pathway mediated by the nuclear receptor LXRα," *Nature*, 383:728–731, 1996.
Javitt et al., "26–hydroxycholesterol," *J. Biol. Chem.*, 256:12644–12646, 1981.
Jelinek et al., "Cloning and regulation of cholesterol 7 alpha–hydroxylase, the rate–limiting enzyme in bile acid biosynthesis," *J. Biol. Chem.*, 265(14):8190–8197, 1990.
Kandutsch et al., "Biological activity of some oxygenated sterols," *Science*, 201:498–501, 1978.
Kliewer et al., "A prostaglandin $J_2$ metabolite binds peroxisome proliferator–activated receptor γ and promotes adipocyte differentiation," *Cell*, 83:813–819, 1995.
Kliewer et al., "Convergence of 9–cis retinoic acid and peroxisome proliferator signalling pathways through heterodimer formation of their receptors," *Nature*, 358:771–774, 1992.
Lala et al., "Activation of the orphan nuclear receptor steroidogenic factor 1 by oxysterols," *Proc. Natl. Acad. Sci. USA*, 94:4895–4900, 1997.

(Continued)

*Primary Examiner*—Michael Pak
(74) *Attorney, Agent, or Firm*—Fulbright & Jaworksi, LLP

(57) ABSTRACT

The present invention provides a method of screening for agonists of an oxycholesterol activator of LXRα transcription, comprising the steps of: introducing a reporter construct and an LXR expression construct into a host cell; treating the host cell with potential LXR-specific ligands; and identifying compounds which activate LXRα transcription. Also provided is a method of screening for antagonists of an oxycholesterol activator of LXRα transcription, comprising the steps of: introducing a reporter construct and an LXR expression construct into a host cell; pretreating the host cell with activators of LXRα transcription; contacting the host cell with potential antagonists of LXRα transcription; and identifying compounds which block the activation the LXRα transcription.

12 Claims, 8 Drawing Sheets

OTHER PUBLICATIONS

Mangelsdorf et al., "The nuclear receptor superfamily: the second decade," *Cell*, 83:835–839, 1995.

Mangelsdorf et al., "Nuclear receptor that identifies a novel retinoic acid response pathway," *Nature*, 345:224–229, 1990.

Morisaki et al., "Studies on steroids. XLV. Synthesis of the four stereoisomers of 20,22–dihydroxycholesterol," *Chem. Pharm. Bull.*, 25:2576–2583, 1977.

Russell, "Ubiquitous receptor: a receptor that modulates gene activation by retinoic acid and thyroid hormone receptors," *Cardiovas. Drugs Ther.*, 6:103–110, 1992.

Song et al., "SREBP–1, a membrane–bound transcription factor released by sterol–regulated proteolysis," *Proc. Natl. Acad. Sci. USA*, 91:10809–10813, 1994.

Wang et al., "The c–erb–A gene encodes a thyroid hormone receptor," *Cell*, 77:53–62, 1994.

Weinberger et al., "LXR, a nuclear receptor that defines a distinct retinoid response pathway," *Nature*, 324:641–646, 1986.

Willy et al., "LXR, a nuclear receptor that defines a distinct retinoid response pathway," *Genes Dev.*, 9:1033–1045, 1995.

Yao et al., "Drosophila ultraspiracle modulates ecdysone receptor function via heterodimer formation," *Cell*, 71:63–72, 1992.

\* cited by examiner

SEQUENCE LISTING

<160> NUMBER OF SEQ ID NOS: 1

<210> SEQ ID NO 1
<211> LENGTH: 34
<212> TYPE: DNA
<213> ORGANISM: Artificial Sequence
<220> FEATURE:
<223> OTHER INFORMATION: Description of Artificial Sequence: Synthetic Primer

<400> SEQUENCE: 1
gcggttccca gggtttaaat aagttcatct agat                34

METHOD OF SCREENING OXYSTEROL ACTIVATION OF LXRα

CROSS-REFERENCE TO RELATED APPLICATION

This is a continuation of application Ser. No. 08/943,936, filed Sep. 26, 1997, now abandoned.

This application claims the benefit of provisional application U.S. Ser. No. 60/026,796, filed Sep. 27, 1996.

BACKGROUND OF THE INVENTION

1. Field of the Invention

The present invention relates generally to the fields of biochemical endocrinology and receptor chemistry. More specifically, the present invention relates to novel oxy-sterol ligands for the LXR receptor and uses thereof.

2. Description of the Related Art

All-trans retinoic acid and 9-cis retinoic acid are metabolites of vitamin A that mediate tissue specific expression of target genes. This is accomplished through binding of two classes of nuclear receptors, the retinoic acid receptors (RARs) and the retinoid X receptors (RXRs). Like other members of the nuclear receptor superfamily, the retinoid receptors transactivate their target genes by binding to specific sites called hormone response elements found within the 5' regulatory region of the target gene.

The highest affinity hormone response elements for the retinoid receptors, as well as the vitamin D receptor (VDR), thyroid hormone receptors (TRs) and peroxisome proliferative activated receptors (PPARs) have been characterized as direct repeats of the canonical hexad, AGGTCA, separated by one to five nucleotides. RAR, VDR, TR and PPAR preferentially bind to their hormone response elements in vitro as heterodimers complexed with RXR. Reconstitution studies in yeast and RXR gene disruption experiments in mice confirm the function of the RXR heterodimer and suggest that it has an obligatory role in vivo as well as in vitro. Thus, RXRs appear to be essential pleiotropic regulators of several signaling pathways.

In terms of retinoid signaling, two distinct pathways are known, the RXR/RAR heterodimer and RXR homodimer. The RXR/RAR heterodimer mediates all-trans retinoic acid or 9-cis retinoic acid action through its high affinity binding to a direct repeat response element having a spacer of 5 nucleotides, i.e., a DR5 element, and to some extent DR2 elements. Recently, it has been shown that when the RXR/RAR heterodimer is bound to DNA, RXR occupies the 5' half-site and RAR occupies the 3' half-site of the DR5 element. In this configuration, RXR is unable to bind ligand and thus functions as a silent partner. The role of RXR as a silent partner is consistent with the finding that other receptors that heterodimerize with RXR do not require 9-cis retinoic acid for their activation.

In the RXR homodimer, RXR acts as its own partner and mediates 9-cis retinoic acid action through binding to DR1 elements. Interestingly, the RXR/RAR heterodimer also binds the DR1 element and does so with higher affinity than the RXR homodimer. The consequence of this binding is that the RXR/RAR heterodimer is a potent repressor of 9-cis retinoic acid activation through the RXR homodimer. These findings suggest that in order for the RXR homodimer to be active, i.e., for RXR to be able to function in vivo as a 9-cis retinoic acid receptor), the ratio of RXR to RAR in a cell must be very high. This may explain why cells that endogenously express RXR and RAR yield significant retinoid responses with DR5 containing reporter genes but do not yield any response with DR1-containing reporter genes, unles RXRs are overexpressed in these cells.

Recently, an orphan member of the nuclear receptor superfamily, named LXRα, in the presence of RXR ligand, e.g., 9-cis retinoic acid, is a potent inducer of transactivation through a distinct retinoid response element. The LXRα response to retinoids is due to the unique interaction of LXRα with endogenous RXR in cells. This interaction permits RXR to work as an active, ligand-binding heterodimeric partner. LXRα has the ability to function as a tissue-specific mediator of a novel retinoid-response pathway.

The prior art is deficient in the lack of the ability to transactivate LXRα in vivo. The prior art is further deficient in the lack of a nuclear receptor signaling pathway for oxysterols and methods to manipulate the use of LXRα as a sensor of cholesterol metabolites. The present invention fulfills this longstanding need and desire in the art.

SUMMARY OF THE INVENTION

Cholesterol and its oxysterol congeners are important constituents of cell membranes and function as intermediates in several crucial biosynthetic pathways. These compounds also autoregulate their metabolic fate by end-product repression and by activation of down-stream catabolism[1]. While end-product repression of transcriptional targets by oxysterols is relatively well understood[2], the mechanism by which these compounds act as positive transcription signaling molecules is unknown. The present invention identifies a specific group of endogenous oxysterols that activate transcription through the nuclear receptor, LXRα. Transactivation of LXRα by oxysterols occurs at concentrations at which these compounds are known to exist in vivo. The most potent activators are sterols that also serve as intermediary substrates in the rate-limiting steps of three important metabolic pathways; a) steroid hormone biosynthesis, b) bile acid synthesis, and c) conversion of lanosterol to cholesterol. The present invention demonstrates the existence of a nuclear signaling pathway for oxysterols and indicates that LXRα likely plays an important role as a sensor of cholesterol metabolites.

In one embodiment of the present invention, there is provided a method of screening for agonists of an oxysterol activator of LXRα transcription, comprising the steps of: introducing a reporter construct and an LXR expression construct into a host cell; treating the host cell with potential LXR-specific ligands; and identifying compounds which activate LXRα transcription.

In another embodiment of the present invention, there is provided a method of screening for antagonists of an oxysterol activator of LXRα transcription, comprising the steps of: introducing a reporter construct and an LXR expression construct into a host cell; pretreating the host cell with activators of LXRα transcription: contacting the host cell with potential antagonists of LXRα transcription; and identifying compounds which block the activation of LXRα transcription.

In another embodiment of the present invention, there is provided a method of enhancing the activation of LXRα transcription in a cell, comprising the step of contacting said cell with a pharmacologically effective dose of an oxysterol, said oxysterol selected from the group consisting of 22(R)-hydroxycholesterol, 20(S)-hydroxycholesterol, 24-hydroxycholesterol, and 25-hydroxycholesterol, 7α-hydroxycholesterol, and FF-MAS.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrated preferred embodiments of the invention and therefore are not to be considered limiting in their scope.

FIG. 3 activation by 22(R)-hydroxycholesterol is LXRα-specific and occurs in a ligand-dependent manner. FIG. 3(A)–3(D) Activation of LXRα by 22(R)-hydroxycholesterol in Drosophila (SL-2) cells. Cells were co-transfected with an LXR responsive reporter plasmid and expression plasmids containing RXRα or LXRα alone, or in combination and then treated with ETOH or 10 μM 22(R)-hydroxycholesterol. (C) Responsiveness to 22(R)-hydroxycholesterol is medicated through the ligand binding domain of LXRα. Shown above the panels are the schematic representations of the LXR-TR and TR-LXR chimeric receptors used in these experiments. CV-1 cells were cotransfected with TK-LXREx3-LUC reporter plasmid and expression plasmids containing the indicated receptor combinations, and then treated with the indicated ligands. (D) The RXR/LXR heterodimer is synergistically activated by 9-cis retinoic acid (9-cis RA) and 22(R)-hydroxycholesterol. CV-1 cells cotransfected with the LXRα expression plasmid and TK-LXREx3-LUC reporter were treated with 9-cis RA, 22(R)-hydroxycholesterol, or both, at the indicated concentrations.

DETAILED DESCRIPTION OF THE INVENTION

Figure 1B:
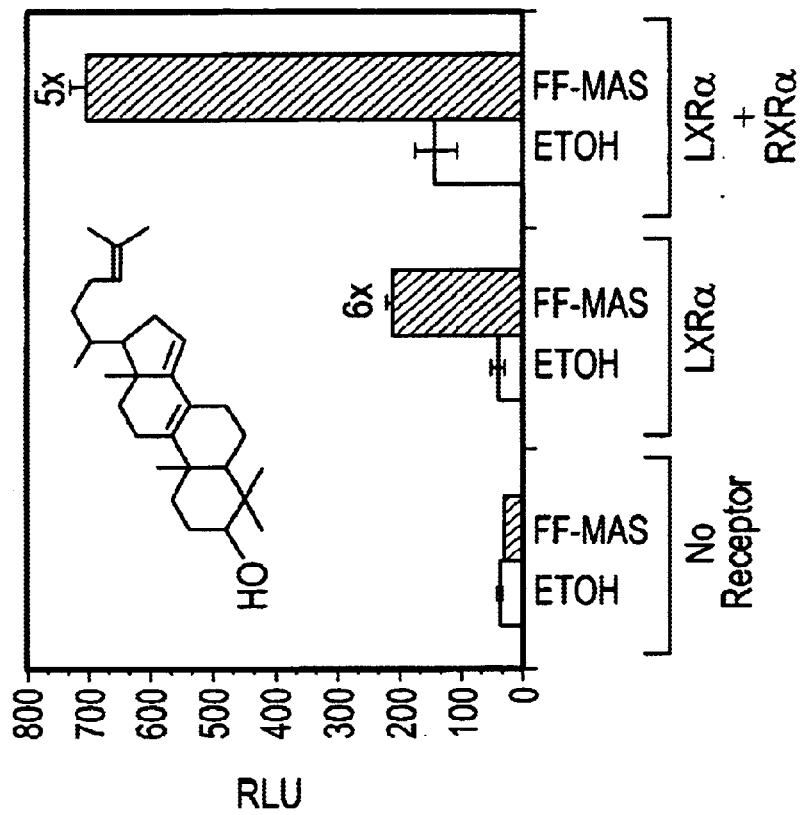
FIG. 1 Human LXRα is activated by gonad sterols. (A) Transactivation of LXRα ligand binding domain (LBD) with testis extract. CV-1 cells were cotransfected with a GAL4 responsive luciferase reporter plasmid and an expression plasmid encoding no receptor or a chimeric receptor composed of the GAL4 DNA binding domain fused to the LXRα ligand binding domain (LBD) (GAL4-LXRα)[3]. After transfection, cells were treated with ethanol (ETOH) or 1% of the concentrated testis extract. (B) Transactivation of LXRα with follicular fluid meiosis activating substance (FF-MAS). CV-1 cells were cotransfected with an LXRα responsive reporter plasmid and the receptor expression plasmids for LXRα alone or with RXRα. After transfection, cells were treated with ETOH or 50 mM FF-MAS. Inset shows the structure of FF-MAS.

The present invention is directed to the use of certain oxy-sterols and their derivatives as ligands for the nuclear receptor, LXR. Further, the present invention is directed to the use of LXR as a means of screening for agonists and antagonists of cholesterol metabolism. More specifically, the present invention discloses that particular derivatives of cholesterol that are hydroxylated on the side chain can selectively activate the nuclear orphan receptor LXR. Activation of LXR leads to a specific increase in transcription of LXR target genes.

These cholesterol derivatives are natural products that are involved at the rate-limiting step of two critical biosynthetic pathways: steroid hormone synthesis and bile acid synthesis. The ability of these compounds to activate transcription through a nuclear receptor suggests that they are important regulators of these two pathways. Thus, these oxysterol compounds function similar to hormones and LXR functions as their receptor and as such both are ideal pharmaceutical targets. Commercially, these oxysterol compounds could be used to regulate cholesterol metabolism and/or steroid biosynthesis directly or as parent compounds for the development of other agonists and/or antagonists of LXR.

The LXR receptor would be used as a tool to screen for pharmaceuticals usefuls as agonists and/or antagonists of LXR.

The present invention represents the first discovery of ligand activators for the orphan receptor, LXR and the first demonstration of a nuclear receptor for oxysterols. Taken together, these findings indicate that LXR is a molecular sensor for the regulation of cholesterol metabolism at a transcriptional level and the signals which directly trigger this sensor are the oxysterol compounds described herein.

Most agents that are currently used to modulate cholesterol in the body are targeted against cholesterol synthesis, transport and cellular uptake. The present invention indicates that a downstream regulatory step exists for the metabolic clearance of cholesterol. Since a receptor mediated process is involved, agonists and antagonists to the LXR ligands can be developed and a person having ordinary skill in this art therefore can specifically manipulate this process using the natural ligands as lead compounds and LXR as a means to screen these compounds for activity. These compounds' ability to serve as the immediate substrate for cholesterol side-chain cleavage (the rate limiting step in steroid hormone biosynthesis) demonstrates that these compounds may be hormonal signals that regulate this pathway. Furthermore, the fact that this pathway is receptor-mediated suggests that it can be directly manipulated by the development of high affinity, high specific activity LXR ligands that are derived from the use of the natural compounds described herein.

The natural LXR ligands are potential drugs or drug targets for the treatment of aberrant cholesterol metabolism and/or steroid hormone biosynthesis. The receptor, LXR, provides a means for identifying and evaluating the activity of such drugs. Specific receptors that bind and direct the upregulated transcriptional responses of cholesterol metabolites in vivo have not been previously identified. The present invention defines both the specific receptor target, i.e., LXR, and also the specific chemical agents responsible for such signalling.

The methods of the present invention may employ a reporter gene that confers on its recombinant hosts a readily detectable phenotype. Generally, reporter genes encode a polypeptide not otherwise produced by the host cell which is detectable by in situ analysis of the cell culture, e.g., by the direct fluorometric, radioisotopic or spectrophotometric analysis of the cell culture without the need to remove the cells for signal analysis from the culture chamber in which they are contained. In one example, the gene may encode an enzyme which produces colorimetric or fluorometric change in the host cell which is detectable by in situ analysis and which is a quantitative or semi-quantitative function of transcriptional activation. Representative examples include esterases, phosphatases, proteases and other enzymes capable of being detected by activity which generates a chromophore or fluorophore as will be known by those individuals having ordinary skill in this art. One well known example is firefly luciferase. Another example is *E. coli* beta-galactosidase, an enzyme which produces a color change upon cleavage of the indigogenic substrate indolyl-B-D-galactoside by cells bearing beta-galactosidase.

Another class of reporter genes which confer detectable characteristics on a host cell are those which encode polypeptides, generally enzymes, which render their transformants resistant against toxins, e.g., the neo gene which protects host cells against toxic levels of the antibiotic G418; a gene encoding dihydrofolate reductase, which confers resistance to methotrexate, or the chloramphenicol acetyltransferase (CAT) gene.

The present invention is directed to a method of screening for agonists of an oxysterol activator of LXR transcription, comprising the steps of: introducing a reporter construct and an LXR expression construct into a host cell; treating the host cell with potential LXR-specific ligands; and identifying compounds which activate LXR transcription. In another embodiment, this method further comprises introducing an RXR expression construct into said host cell.

In this method of screening for agonists of an oxysterol activator of LXR transcription of the present invention, the LXR expression construct is selected from the group consisting of CMX-LXR, CMX-gal-LXR, RSV-LXR and A5C-LXR. Preferred forms of LXR include human, rat or mouse LXR in the methods of the present invention. Representative nuclear receptors include the retinoic acid receptor, vitamin D receptor, thyroid hormone receptor, estrogen receptor, the progesterone receptor, farnesol (FXR) receptor, ecdysone receptor and the PPAR receptor.

In this method of of screening for agonists of an oxysterol activator of LXR transcription the present invention, the host cell is selected from the group consisting of mammalian cells, such as CV1, HeLa, HepG2, COS, 293, F9, 3T3 and drosophila cell such as Schneider SL2. A person having ordinary skill would readily recognize that other host cell may be used.

In this method of screening for agonists of an oxysterol activator of LXR transcription of the present invention, the reporter construct is selected from the group consisting of TK-LXRE-LUC, TK-LXRE-CAT, ADH-LXRE-LUC, ADH-LXRE-CAT, TK-gal4$_{UAS}$-LUC, TK-gal4$_{UAS}$-CAT. These latter 2 reporter constructs would be used with the expression construct described above containing gal4.

In this method of screening for agonists of an oxysterol activator of LXR transcription the present invention, the means to identify compounds which activate LXRα transcription construct would be well known to those having ordinary skill in this art. Preferred means to identify compounds which LXRα transcription are selected from the group consisting of luciferase assay, a CAT assay, a beta-galactosidase assay, measuring reporter enzyme levels using such instrument or techniques as luminometer, spectrophotometer and thin layer chromatography.

In another method of the present invention, one may screen for antagonists of an oxycholesterol activator of LXRα transcription. This method comprises the steps of: introducing a reporter construct and an LXR expression construct into a host cell; pretreating the host cell with an activator of LXRα transcription; contacting the host cell with potential antagonists of LXRα transcription; and identifying compounds which block the activation of LXRα transcription.

In this method of screening for antagonists of an oxysterol activator of LXR transcription of the present invention, the LXR expression construct is selected from the group consisting of CMX-LXR, CMX-gal-LXR, RSV-LXR and A5C-LXR. Preferred forms of LXR include human rat or mouse LXR in the methods of the present invention. Representative nuclear receptors include the retinoic acid receptor, vitamin D receptor, thyroid hormone receptor, estrogen receptor, the progesterone receptor, farnesol (FXR) receptor, ecdysone receptor and the PPAR receptor.

In this method of screening for antagonists of an oxysterol activator of LXR transcription the present invention, the host cell is selected from the group consisting of mammalian cells, such as CV1, HeLa, HepG2, COS, 293, F9, 3T3 and drosophila cell such as Schneider SL2. A person having ordinary skill would readily recognize that other host cell may be used.

In this method of screening for antagonists of an oxysterol activator of LXR transcription of the present invention, the reporter construct is selected from the group consisting of TK-LXRE-LUC, TK-LXRE-CAT, ADH-LXRE-LUC, ADH-LXRE-CAT, TK-gal4$_{UAS}$-LUC, TK-gal4$_{UAS}$-CAT. These latter two reporter constructs would be used with the expression construct described above containing gal4.

In this method of screening for antagonists of an oxysterol activator of LXR transcription the present invention, the means to identify compounds which block the activatation of LXRα transcription would be well known to those having ordinary skill in this art. Preferred means to identify compounds which LXRα transcription are selected from the group consisting of luciferase assay, a CAT assay, a beta-galactosidase assay, measuring reporter enzyme levels using such instrument or techniques as luminometer, spectrophotometer and thin layer chromatography.

The following examples are given for the purpose of illustrating various embodiments of the invention and are not meant to limit the present invention in any fashion.

EXAMPLE 1

Effect of bull testis extract and FF-MAS on transcription of LXRα

Organic extraction of breeding bull testis was performed as described[6]. Briefly, 12 grams of lyophilized testis was extracted with N-heptane and lipids were concentrated by roto-evaporation. Aliquots representing 1% of this material were assayed. FF-MAS was synthesized as described[18]. Transient transfections in CV-1 monkey kidney cells were performed in triplicate in 48-well plates as described[3] with media containing 5% cabosil-treated calf bovine serum.

Figure 1A:
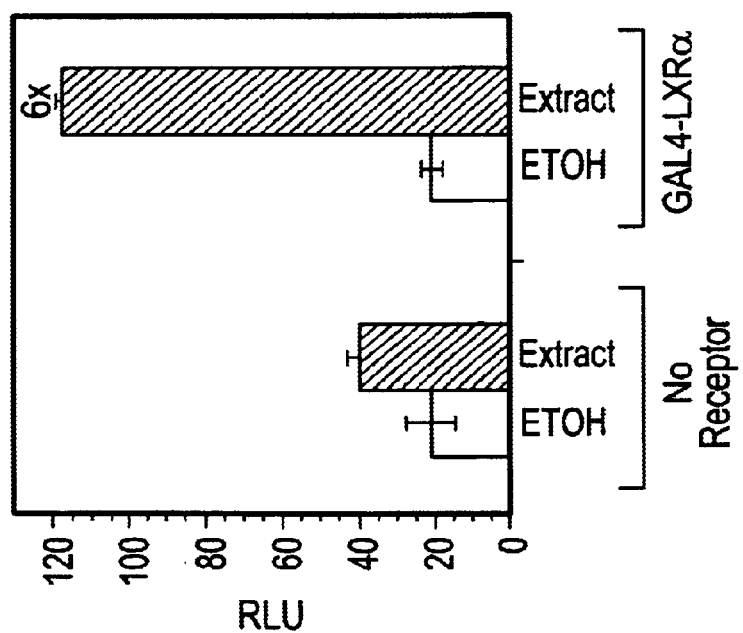

Transfections were performed in FIG. 1A using 80 ng of TK-MH100x4-LUC reporter and 30 ng of CMX-GAL4-hLXRα expression plasmids per well; and in FIG. 1B using 50 ng of TK-LXREx3-LUC reporter and 25 ng of CMX-hLXRa alone or with 25 ng CMX-hRXRa expression plasmids per well. Candidate ligands were dissolved in ethanol and added 8 hours post-transfection. As an internal standard, 50 ng of CMX-β gal was included in all transfections. All plasmid constructs and determinations of luciferase and β-galactosidase activities have been described[3]. To construct CMX-LXRα, the hLXRα cDNA insert was excised from the plasmid pXR2DRV (Willy, et al., 1995, *Genes Dev.* 9: 1033–1045) with Kpnl and BamHI and was ligated into the expression vector CMX. CMX-βgal was constructed by ligating the β-galactosidase gene into the expression vector CMX. Chimeric Gal4-receptor expression plasmid (CMX-GAL4-LXRα) was constructed by first ligating the GAL4 portion of pSC424 (Sadowski, I. and M. Ptashne, 1989, *Nucleic Acids Res.* 19: 7539–7530) into the HindIII/SacI sites of pCMX (Umesono, et al., 1991, *Cell* 65: 1255–1266) to create pCMX-GAL4. This vector contains the CMV promoter fused to the coding sequence for GAL4 (1–147), followed by inframe polylinker cloning sites and translational stop codons. The cDNAs encoding the ligand-binding domain (LBD) of hLXRα (amino acids 166–447) was then ligated into the polylinker to create CMX-GAL4-LXRα.

Reporter plasmids for these studies were constructed by ligating the appropriate oligonucleotides into the HindIII site of the TK-LUC vector to create TK-LXREx3-LUC, TK-MH100x4-LUC (Kang, T., et al., 1993, *J. Biol Chem.* 268: 9629–9635). The sense strand of the LXRE oligonucleotide used to construct the reporter plasmid TK-LXREx3-LUC was 5'agcttGCGGTTCCCAGGGTT-TAAATAAGTTCATCTAGAT3' (SEQ. ID. NO. 1). All constructs were verified by sequencing. Data are presented as relative light units (RLUs) and represent the mean of triplicate assays±standard error.

Human LXRα is an orphan member of the nuclear receptor superfamily that has the potential to function as a ligand-dependent transcription factor when complexed with its heterodimeric partner, the retinoid X receptor (RXR)[3]. To identify LXRα ligands, concentrated lipid extracts from a variety of tissues were prepared and tested for an ability to activate LXRα in a high throughput cotransfection assay similar to that used to identify ligands for other receptors[4,5]. For the initial screening, a chimeric receptor was used in which the ligand binding domain of LXRα was fused to the DNA binding domain of the yeast transcription factor GAL4[3]. The resultant GAL4-LXRα expression plasmid was cotransfected along with a GAL4-responsive luciferase reporter plasmid into CV-1 cells and challenged with concentrates from several tissues sources.

In the βgal and luciferase assays, cells were harvested 36 hours after addition of ligand, lysed, and the cytosols analyzed for luciferase and β-galactosidase activity using a Dynatech microtiter plate model ML3000 luminometer and a model MR5000 spectrophotometer, respectively. All transfection data points were normalized to the internal β-galactosidase marker (Mangelsdorf et al., 1990) and are the mean of triplicate assays±standard error.

A significant (6 fold) induction of luciferase activity was seen with extracts derived from breeding bull testis (FIG. 1A). The migration of this lipid activity on reverse phase HPLC (data not shown) suggested that the compound might be related to a class of sterols, termed meiosis activating sterols (MAS), recently isolated from gonads[6].

To demonstrate that these sterols were LXRα activators, one of these compounds, FF-MAS (FIG. 1B, inset), was synthesized de novo and tested in the cotransfection assay using wild-type LXRα and a luciferase reporter plasmid containing the LXR response element (TK-LXREx3-LUC)[3]. In agreement with the results from testis extracts, a 5–6 fold induction of transcription by LXRα was seen in the presence of FF-MAS (FIG. 1B). Expression of RXRα above the endogenous level in CV-1 cells results in an enhancement of the LXRα response, consistent with the finding that LXRα and RXRα form an obligate heterodimer[3].

EXAMPLE 2

Specific oxysterol activatation of LXRα

27-hydroxycholesterol was obtained from Dr. Norman Javitt; 24-hydroxycholesterol was obtained from Drs. Erik Lund and David Russell; 7α,25-dihydroxycholesterol was obtained from Drs. Margrit Schwarz and David Russell; isomers of 20,22-hydroxycholesterol were synthesized as described[19] or obtained from Dr. J. Mason. All other sterols were purchased from Steraloids, Inc. (Wilton, N.H.) or Research Plus, Inc. (Bayonne, N.J.); all steroid hormones and other receptor ligands were purchased from Sigma (St. Louis, Mo.).

Figure 2A:
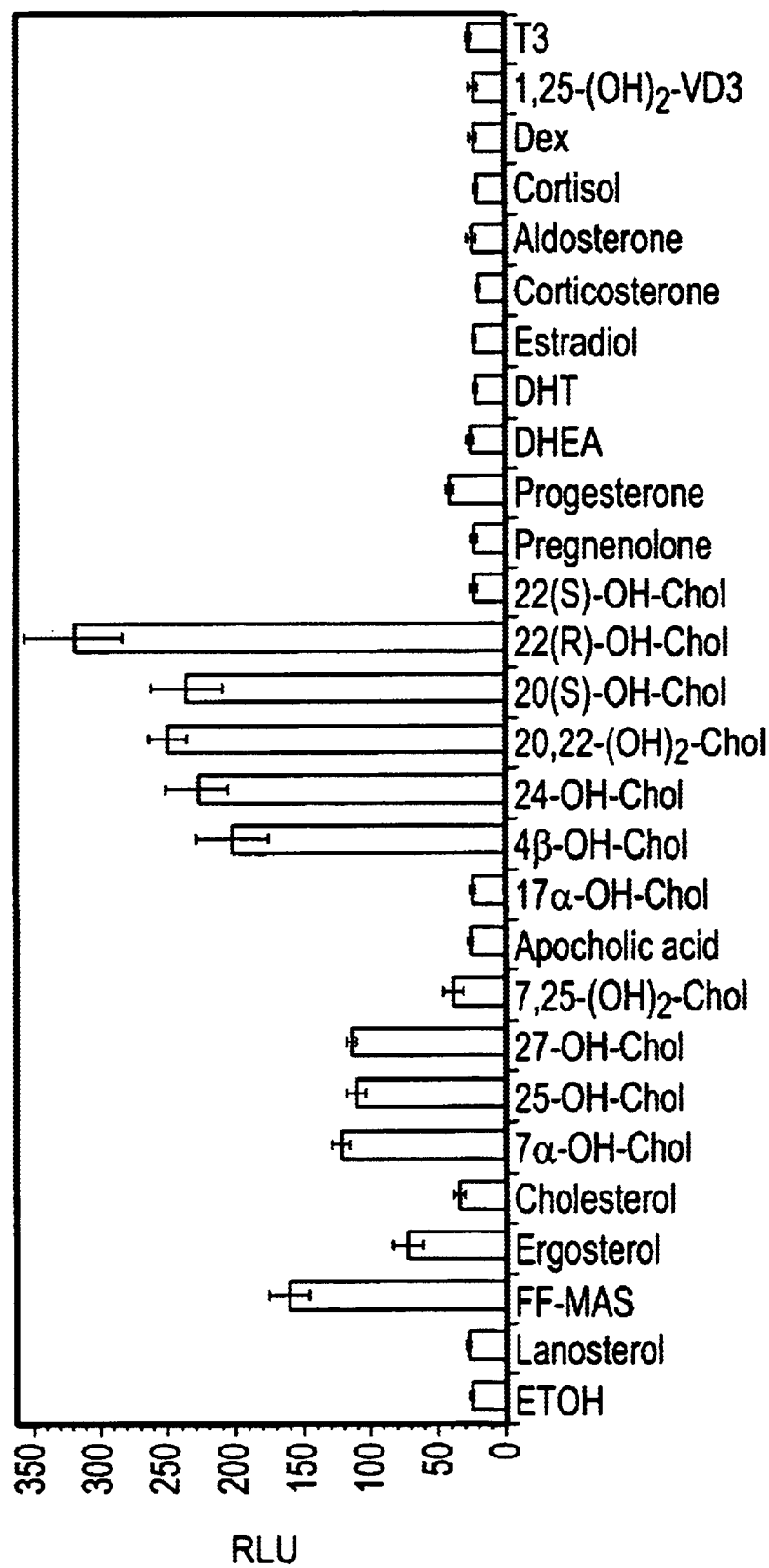
FIG. 2 LXRα is activated by a specific subset of oxysterols. (A) Specificity of LXRα activators. Shown is a representative group from 70 compounds evaluated for LXRα activity (10 μM) in cotransfection assays as described in FIG. 1B. In addition to the compounds shown, farnesol fatty acids, and lanosterol precursors had no LXRα activity. (B) The the structure-activity relationship of LXRα activators. Data compiled from FIG. 2A and other experiments (not shown) reveal that the position of the hydroxyl on the cholesterol backbone is a determinant of LXRα activity. Circles and squares represent the positions at which hydroxyl groups render the compound active or inactive, respectively. (C) Compound 22(R)-hydroxycholesterol (HC) is the most potent LXRα activator. Dose response curves for LXRα activators were generated in CV-1 cell cotransfection assays as described in FIG. 1B. The $EC_{50}$ for LXRα activators are 1.5 μM 22(R)-hydroxycholesterol, 1.6 μM 20(S)-hydroxycholesterol, 1.6 μM 24-hydroxycholesterol, and 3.5 μM 25-hydroxycholesterol, 7β-hydroxycholesterol, and FF-MAS.

In addition to regulating meiosis, FF-MAS is a biosynthetic precursor to cholesterol. The ability of FF-MAS to specifically induce LXRα transactivation led to an examination of related compounds in the cholesterol metabolic pathway which might also activate LXRα. Over 70 compounds were tested, including the known nuclear receptor ligands and several intermediates in the biosynthetic pathways leading to cholesterol, steroid hormones, and bile acids. Remarkably, only a specific group of oxysterols were observed to activate (5 to 15-fold) LXRα (FIG. 2A).

Figure 2B:
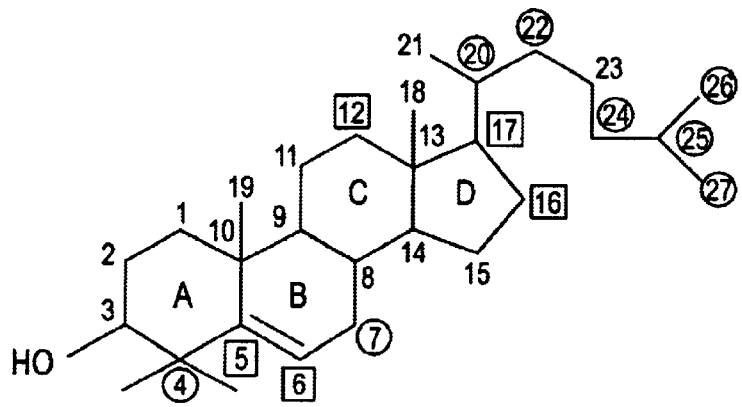

EXAMPLE 3
Structure-activity relationships of oxysterol activators of LXRα transcription The structure-activity relationships of these compounds reveal a requirement for the 3β-hydroxyl group of cholesterol and an additional hydroxyl group preferentially located on the side chain of the molecule (FIG. 2B). The strongest LXRα activator is a naturally occurring compound, 22(R)-hydroxycholesterol 22(R)-hydroxycholesterol. Significantly, the S enantiomer of this molecule 22(S)-hydroxycholesterol is completely inactive (FIG. 2A). Thus, both the precise location and the stereochemistry of the hyroxyl are important for activity.

Figure 2C:
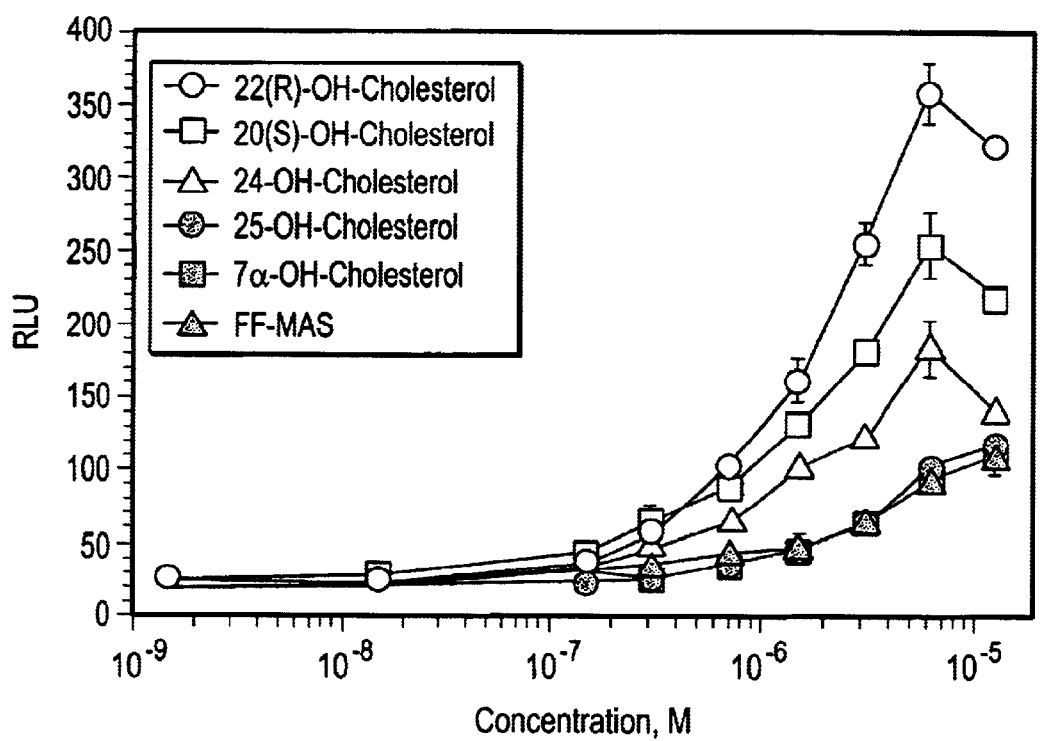

The position of the second hydroxyl group allows a distinct rank order of potency to be assigned 22(R)-hyroxycholesterol>20(S)-hydroxycholesterol>24-hydroxycholesterol>25-hydroxycholesterol=7α-hydroxycholesterol=FF-MAS), with 22(R)-hydroxycholesterol giving the most potent, saturable response ($EC_{50}$=1.5 μM, FIG. 2C). The concentrations at which these sterols are able to elicit an LXRα response are within their known physiological range[7-10]. Furthermore, these concentrations are at or below those required for ligand-dependent activation of other nuclear receptors (e.g., FXR and PPAR)[11-13] and the sterol-mediated repression of transcription modulated by sterol regulatory element binding proteins (i.e., SREBPs)[2]. These observations are strong evidence that these sterols may function as physiologically relevant activators of LXRα.

Figure 3A:
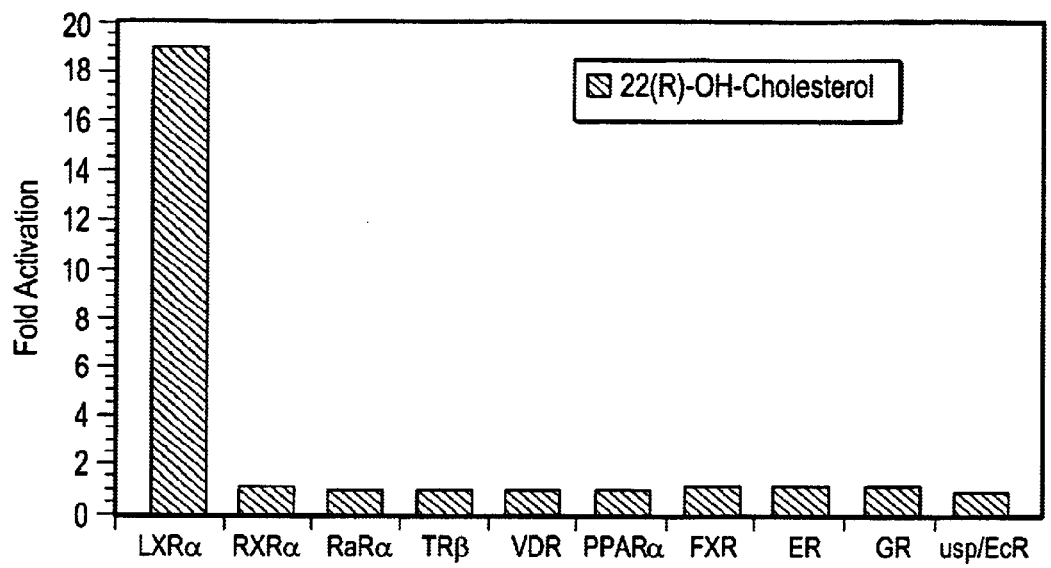
FIG. 3A shows the receptor-specific transactivation by 22(R)-hydroxycholesterol. CV-1 cells were cotransfected with the following expression plasmids containing various nuclear receptors and luciferase reporters containing their cognate response elements[16]; human LXRα, TK-LXREx3-LUC; TK-LXREx3-LUX; human retinoid X receptor-α (RXRα)[21], TK-CRBPH-LUC; human retinoic acid receptor-α (RARα)[22], TK-DR5-LUC; human thyroid hormone receptor-β (TRβ)[23], TK-DR-4-LUC; human vitamin D receptor (VDR)[24], TK-DR[3]-LUC; human peroxisome proliferator-activated receptor-α (PPARα)[25], TK-PPREx3-LUC; human farnesol activated receptor (FXR)[11], ΔMTV-EcREx5-LUC; human estrogen receptor (ER)[26], ΔMTV-ERE-LUC; human glucocorticoid receptor (GR)[27], MTV-LUC; Drosophila ecdysone receptor (usp/EcR)[15], ΔMTV-EcREx5-LUC. Cells were treated with ETOH or 6 μM 22(R)-hydroxycholesterol. Data are expressed as the fold induction of 22(R)-hydroxycholesterol-induced activation over ETOH controls. As a positive control for each receptor, cells were treated with saturating concentrations of their cognate ligands (data not shown).
Figure 3B:
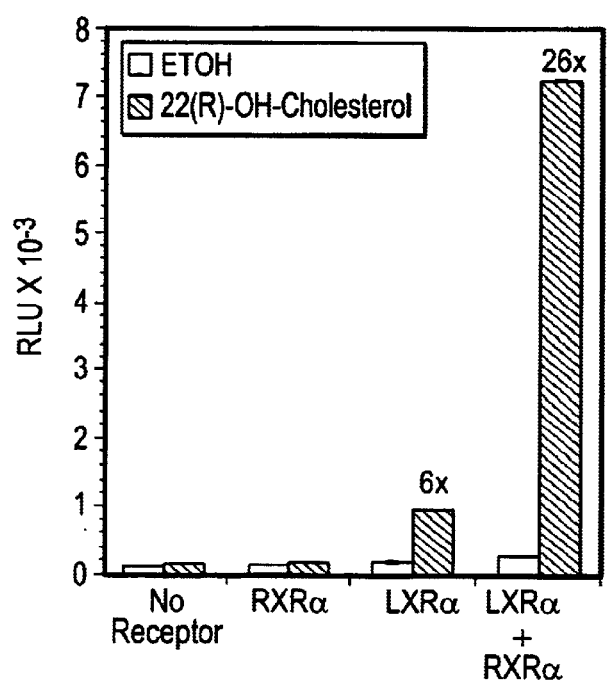
Figure 3C:
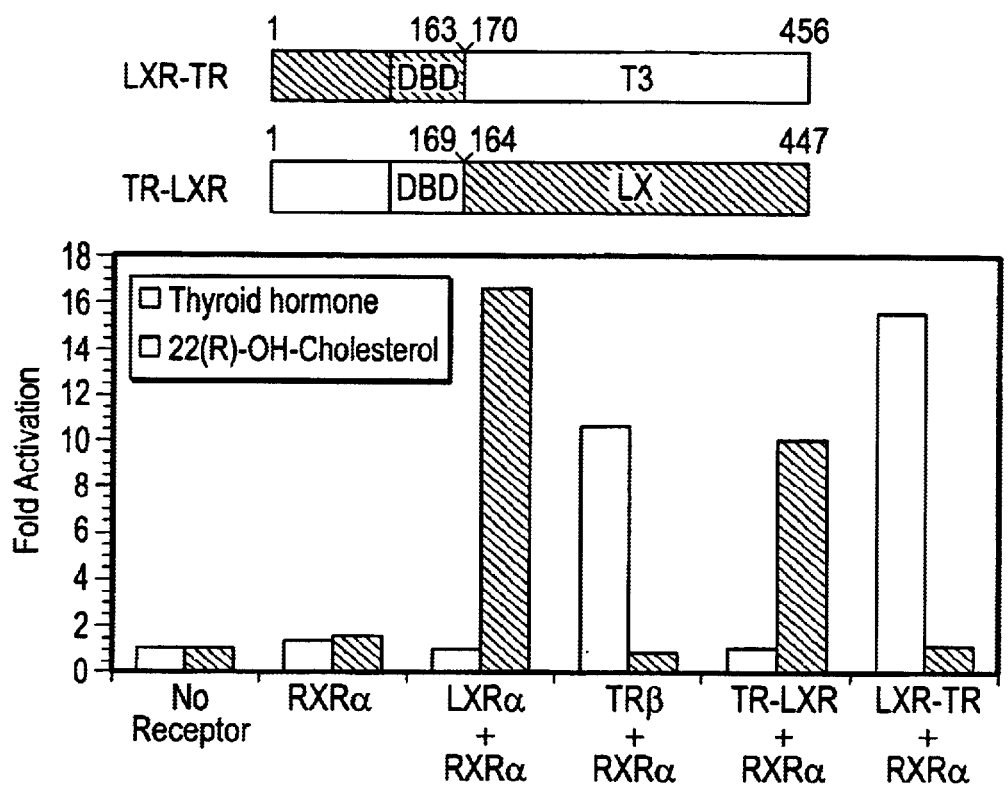

EXAMPLE 4
Specificity of the LXRα transactivation activator 22(R)-hydroxycholesterol All transfection assays were performed in triplicate as described in FIG. 1B. In FIG. 3B. Drosophila SL-2 cells were transfected and assayed as previously described[5] in 6-well plates with 1 mg A5C-hLXRα or A5C-hLXRα, 0.5 mg ADH-LXREx2-LUC, 0.2 mg A5C-βGAL and 8 mg PGEM4 carrier DNA per well. In FIG. 3C, chimeric receptors were constructed by fusing the cDNA encoding the human LXRα N-terminus and DNA binding domain (amino acids 1–163) with the ligand binding domain of human TRβ (amino acids 170–456) to make CMX-hLXR-TR, and by fusing the cDNA encoding the TRβ N-terminus and DNA binding domain (amino acids 1–169) with the ligand binding domain of LXRα (amino acids 164–447) to make CMX-hTR-LXR.

The unique structure-activity relationships for the LXRα activators described above are a hallmark feature of a receptor-mediated response. Consistent with this notion, transactivation by the most potent activator, 22(R)-hydroxycholesterol, is LXRα specific and shows no cross-reactivity with a variety of other known nuclear receptors (FIG. 3A). This activity requires both LXRα and its response element, and is not observed on response elements of other nuclear receptors (data not shown).

EXAMPLE 5
Co-transfection of LXRα with RXRα

To further demonstrate that the oxysterol response is LXRα-dependent, whether this pathway could be recapitulated in a heterologous system was examined. The insect cell line, SL-2, which lacks mammalian nuclear receptors and is deficient in the metabolic pathways for cholesterol and bile acid synthesis[14], was used as a transfection host in these experiments. These cells contain ultraspiracle[15], an RXR homologue that can form a functional heterodimer with LXRα on its response element (data not shown). Consequently, transfection of XLRα alone into SL-2 cells results in a 6-fold induction by 22(R)-hydroxycholesterol (FIG. 3B). As expected, when RXRα is cotransfected with LXRα, a robust (26-fold) increase in 22(R)-hydroxycholesterol induction occurs (FIG. 3B). Taken together, these data illustrate that LXRα directly mediates the 22(R)-hydroxycholesterol transcriptional response.

EXAMPLE 6
Requirement of LBD of LXRα for sterol responsiveness

One characteristic of all ligand activated nuclear receptors is the presence of a functionally transferable ligand binding domain[16]. To examine such a domain in LXRα that is responsive to 22(R)-hydroxycholesterol, two chimeric receptors (TR-LXR and LXR-TR) were expressed in which the ligand binding domain of the thyroid hormone receptor (TRβ) and the corresponding region of LXRα were exchanged (FIG. 3C). TRβ was chosen for these studies because both TRβ and LXRα can bind and transactivate the same response element (i.e., the LXRE)[3].

As RXR heterodimers, LXRα and TRβ respond to their cognate ligands (FIG. 3C). However, when the amino terminus and DNA binding domain of TRβ are fused to the putative ligand binding domain of LXRα, the resultant TR-LXR chimera responded to 22(R)-hydroxycholesterol, but not thyroid hormone (FIG. 3C). The reciprocal chimera, LXR-TR loses responsiveness to 22(R)-hydroxycholesterol, but gains responsiveness to thyroid hormone. These experiments demonstrate that the ligand binding domain of LXRα is required for sterol responsiveness and that this region alone can transfer sterol inducibility to another protein, further supporting the proposal that LXRα is a sterol responsive receptor.

Figure 3D:
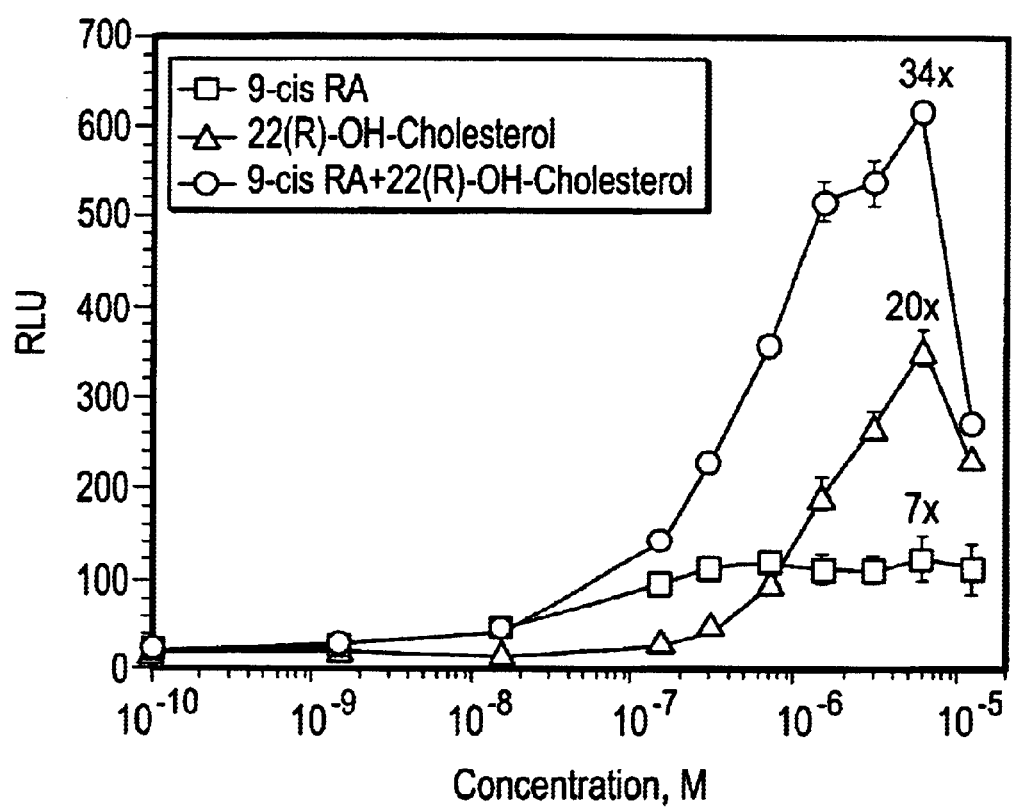

A subset of receptors that function as RXR heterodimers have the unique ability to be activated by their own ligand, the RXR ligand (i.e., 9-cis retinoic acid), or both ligands together[11,17]. The RXR/LXR heterodimer falls into this category of receptors, since this heterodimer can be activated by 9-cis retinoic acid or 22(R)-hydroxycholesterol in a dose-dependent manner, with maximal inductions of 7-fold and 20-fold, respectively (FIG. 3D). Significantly, even at suboptimal concentrations, activation by both compounds together is more than additive, achieving a maximum induction of greater than 30-fold. These results are consistent with each receptor within the RXR/LXR heterodimer being activated by their respective ligand.

EXAMPLE 7
Protease protection assay

In vitro synthesized [$^{35}$S]-labelled Flag-LXRα protein was subjected to protease digestion with α-chymotrysin. For these studies, LXRα with a Flag epitope fused to the amino terminus was used. The Flag epitope increases the efficiency of translation and does not interfere with LXRα activity as determined by DNA binding and transfection studies.

Figures 4A, 4B:
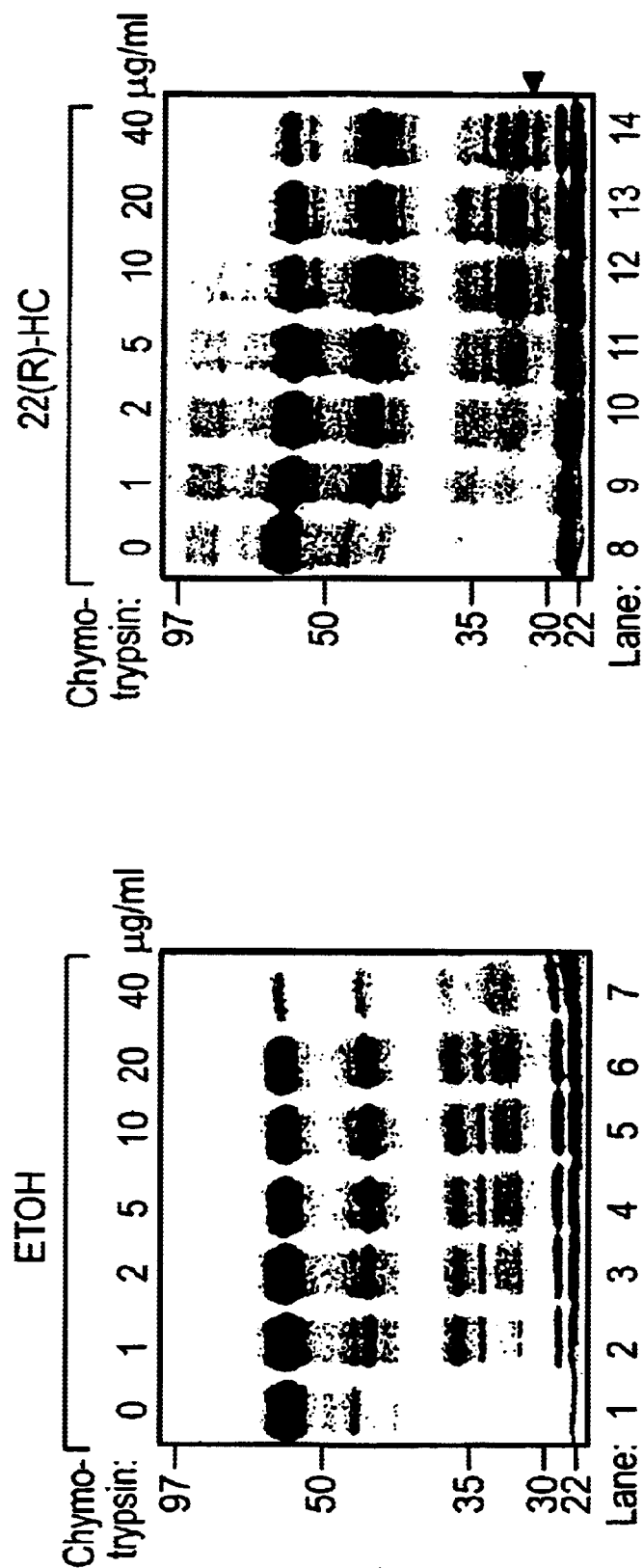
FIG. 4, Protease protection of LXRα with 22(R)-hydroxycholesterol. [$^{35}$S]-labelled LXRα protein was incubated with (A) ethanol (ETOH) control or (B) 22(R)-hydroxycholesterol, subjected to protease digestion with increasing amounts of chymotrypsin, and analyzed by SDS-PAGE and autoradiography. The arrowhead depicts a novel digestion product specifically protected by 22(R)-hydroxycholesterol.

The unavailability of radiolabelled LXRα activators prevents direct ligand binding analysis. To address the possibility that 22(R)-hydroxycholesterol interacts with LXRα, a limited protease protection assay was performed (FIG. 4). In this experiment, several proteolytic fragments were generated when LXRα protein was incubated with increasing concentrations of the protease, chymotrypsin. Of these fragments, only a unique 30 kDa fragment (arrow in FIG. 4, right panel) was consistently observed in the presence of 22(R)-hydroxycholesterol but not ethanol (FIG. 4, left panel) or 9-cis retinoic acid and cholesterol (data not shown). The presence of a specific ligand-protected ~30 kDa fragment has also been observed during similar analyses with other nuclear receptors. Thus, these protease protection studies support the finding that 22(R)-hydroxycholesterol interacts with LXRα.

Figure 5:
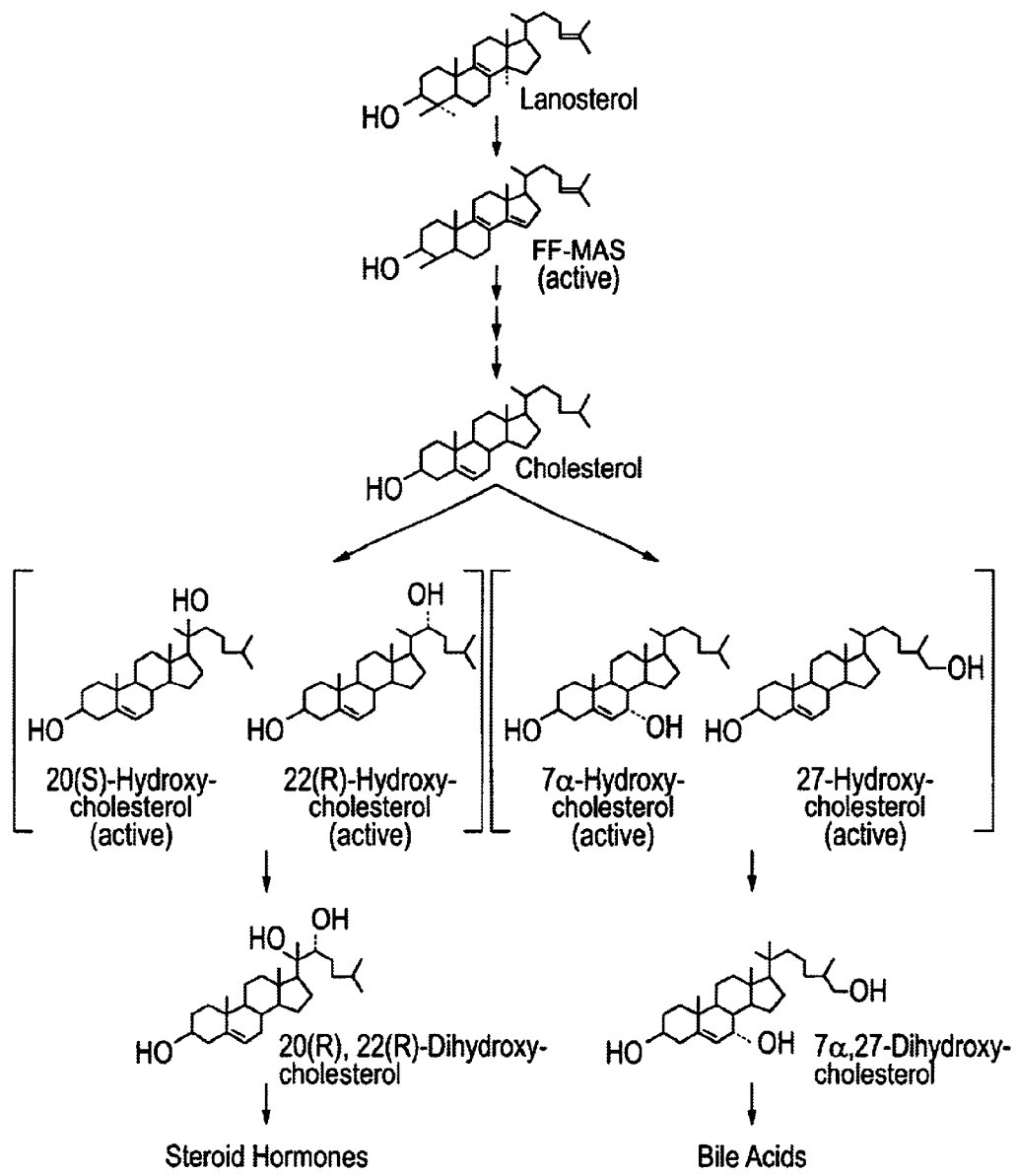
FIG. 5 Metabolic fates of oxysterols. LXRα activators follicular fluid meiosis activating substance, 20(S)-hydroxycholesterol, 22(R)-hydroxycholesterol, 7α-hydroxycholesterol, and 27-hydroxycholesterol are positioned at the rate-limiting steps of three important metabolic pathways; conversion of lanosterol to cholesterol, steroid hormone synthesis, and bile acid synthesis.

The ability of oxysterols to activate transcription through the nuclear receptor LXRα has several implications for the function of these compounds in vivo. Their rank order of potency is distinct from that which modulates end-product repression of cholesterol through SREBP, suggesting that these sterols will have novel functions are activators. For example, FF-MAS has been shown to regulate meiosis[6], suggesting that LXRα or related receptors may function in the gonads. Further clues to the function of these sterols may come from an inspection of their metabolic fates (FIG. 5). LXRα activators exist at the rate-limiting steps of three important pathways: steroid hormone biosynthesis, bile acid synthesis, and conversion of lanosterol to cholesterol. While further metabolism may yield more potent activators, the present invention clearly demonstrates that the immediate upstream and downstream metabolites of these activators (FIG. 4) are significantly less potent (FIG. 2A), implying that compounds such as 22(R)-hydroxycholesterol function as ligands.

Studies to synthesize radiolabeled compounds addresses ligand binding properties. In many metabolic pathways, modulation of the rate-limiting steps is often accomplished by feed-back or feed-forward regulatory loops. LXRα may act as a sensor of specific sterols (e.g. 22(R)-hydroxycholesterol) and thereby transcriptionally regulate a crucial metabolic pathway (e.g., steroid hormone biosynthesis). Consistent with this, the pattern of expression of LXRα is specific to tissues where these pathways exist, such as liver, intestine, and adrenals[3]. That LXRα mediates oxysterol-induced transactivation suggests that, as is the case with retinoids and steroids, a specific class of nuclear receptors exists for oxysterols.

The following references were cited herein:
1. Russell, D., *Cardiovascular Drugs and Therapy* 6, 103–110 (1992).
2. Wang, et al., *Cell* 77, 53–62 (1994).
3. Willy, et al., *Genes Dev.* 9, 1033–1045 (1995).
4. Heyman, et al., *Cell* 68, 397–406 (1992).
5. Harmon, et al., *Proc. Natl. Acad. Sci. USA* 92, 6157–6160 (1995).
6. Byskov, et al., *Nature* 374, 559–562 (1995).
7. Kandutsch, et al., *Science* 201, 498–501 (1978).
8. Dhar, et al., *J. Neurochem.* 21, 51–60 (1973).
9. Javitt, et al., *J. Biol. Chem.* 256, 12644–12646 (1981).
10. Dixon, et al., *Biochem. Biophys. Res. Commun.* 40, 161–165 (1970).
11. Forman, et al., *Cell* 81, 687–693 (1995).
12. Forman, et al., *Cell* 83, 803–812 (1995).
13. Kliewer, et al., *Cell* 83, 813–819 (1995).
14. Ikekawa, N. in *Sterols and bile acids* (eds Danielsson, H.) 199–230 (Elsevier/North Holland Biomedical Press, Amsterdam, 1985).
15. Yao, et al., *Cell* 71, 63–72 (1992).
16. Mangelsdorf, et al., *Cell* 83, 835–839 (1995).
17. Kliewer, et al., *Nature* 358, 771–774 (1992).
18. Dolle, et al., *J. Am. Chem. Soc.* 111, 278–284 (1989).
19. Morisaki, et al., *Chem. Pharm. Bull.* 25, 2576–2583 (1977).
20. Song, et al., *Proc. Natl. Acad. Sci. USA* 91, 10809–10813 (1994).
21. Mangelsdorf, et al., *Nature* 345, 224–229 (1990).
22. Gignère, et al., *Nature* 330, 624–629 (1987).
23. Weinberger, et al., *Nature* 324, 641–646 (1986).
24. Baker, et al., *Proc. Natl. Acad. Sci. USA* 85, 3294–3298 (1988).
25. Issemann, J. & Green, S. *Nature* 347, 645–650 (1990).
26. Green, et al., *Nature* 320, 134–139 (1986).
27. Hollenberg, et al., *Nature* 318, 635–641 (1985).

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of screening for an oxysterol that activates LXRα mediated transcription, comprising the steps of:
   (a) introducing a reporter construct and a human LXRα expression construct into a host cell, wherein transcription of said reporter construct is activated when an oxysterol activator of LXRα binds to the human LXRα protein;
   (b) treating the host cell with a candidate oxysterol activator of LXRα; and
   (c) determining whether said candidate activates human LXRα mediated transcription of said reporter construct,
   wherein activation of reporter construct transcription indicates that said oxysterol activates human LXRα mediated transcription.

2. The method of claim 1, wherein said host cell is selected from the group consisting of mammalian cells and Drosophila cells.

3. The method of claim 2, wherein said mammalian cells are selected from the group consisting of CV1, HeLa, HepG2, COS, 293, F9, and 3T3.

4. The method of claim 1, wherein said determining step comprises a luciferase assay, a CAT assay, a beta-galactosidase assay, or measuring reporter enzyme activity.

5. The method of claim 4, wherein measuring reporter enzyme activity comprises using a luminometer, a spectrophotometer or thin layer chromatography.

6. The method of claim 1, wherein said candidate oxysterol activator of LXRα is a derivative of 22(R)-hydroxycholesterol, 20(S)-hydroxycholesterol, 24-hydroxycholesterol, 25-hydroxycholesterol, 7α-hydroxycholesterol or FF-MAS (follicular fluid meiosis activating substance).

7. The method of claim 6, wherein said derivative is hydroxylated on one or more carbon atoms in the cholesterol backbone of said oxysterol activator, selected from carbon atoms numbered 4, 7, 20, 24, 25, 26 or 27 (FIG. 2B).

8. A method of screening for an oxysterol that activates human LXRα mediated transcription, comprising the steps of:
   (a) providing a host cell comprising a reporter construct and a human LXRα expression construct, wherein transcription of said reporter construct is activated when an oxysterol activator of LXRα binds to the human LXRα protein;
   (b) treating the host cell with a candidate oxysterol activator of LXRα mediated transcription; and
   (c) determining whether said oxysterol activates human LXRα mediated transcription of said reporter construct, wherein activation of reporter construct transcription indicates that said oxysterol is an activator of human LXRα mediated transcription.

9. A method of screening for an oxysterol that activates human LXRα mediated transcription, comprising the steps of:
   (a) providing a host cell comprising a reporter construct and an expression construct, said expression construct comprising a gene encoding a human LXRα protein, wherein transcription of said reporter construct is activated when an oxysterol activator of LXRα binds to the human LXRα protein;
   (b) treating the host cell with an oxysterol; and
   (c) determining whether said oxysterol activates human LXRα mediated transcription of said reporter construct,
   wherein activation of reporter construct transcription indicates that said oxysterol activates human LXRα mediated transcription.

10. The method of claim 9, wherein said oxysterol is a derivative of 22(R)-hydroxycholesterol, 20(S)-hydroxycholesterol, 24-hydroxycholesterol, 25-hydroxycholesterol, 7α-hydroxycholesterol or FF-MAS (follicular fluid meiosis activating substance).

11. The method of claim 10, wherein said derivative is hydroxylated on one or more carbon atoms in the cholesterol backbone of said oxysterol, selected from carbon atoms numbered 4, 7, 20, 22, 24, 25, 26 or 27 (FIG. 2B).

12. The method of claim 1, wherein said human LXRα expression construct is selected from the group consisting of CMX-LXRα, CMX-GAL4-LXRα and A5C-LXRα.

* * * * *